US006488913B2

(12) United States Patent
Orlowski et al.

(10) Patent No.: US 6,488,913 B2
(45) Date of Patent: Dec. 3, 2002

(54) TWO-PART COMPOSITION FOR HIGH EFFICACY TEETH WHITENING COMPRISING A MIXTURE OF PEROXIDES AND/OR PERCARBONATES OF METALS

(75) Inventors: Jan A. Orlowski, Altadena, CA (US); David V. Butler, West Covina, CA (US)

(73) Assignee: Scientific Pharmaceuticals, INC, Pomona, CA (US)

( * ) Notice: Subject to any disclaimer, the term of this patent is extended or adjusted under 35 U.S.C. 154(b) by 0 days.

(21) Appl. No.: 09/931,275

(22) Filed: Aug. 16, 2001

(65) Prior Publication Data

US 2002/0106335 A1 Aug. 8, 2002

Related U.S. Application Data

(60) Provisional application No. 60/234,007, filed on Sep. 20, 2000.

(51) Int. Cl.[7] .......................... A61K 7/20; A61K 33/40; A61K 6/00; A61C 15/00
(52) U.S. Cl. .................. 424/53; 424/613; 424/614; 424/616; 433/215; 433/216
(58) Field of Search ............... 424/53; 433/215, 433/216

(56) References Cited

U.S. PATENT DOCUMENTS

| 4,302,441 A | | 11/1981 | Mühlemann et al. | |
|---|---|---|---|---|
| 4,405,599 A | | 9/1983 | Smigel | |
| 4,522,805 A | | 6/1985 | Gordon | |
| 4,661,070 A | | 4/1987 | Friedman | |
| 4,687,663 A | | 8/1987 | Schaeffer | |
| 4,788,052 A | | 11/1988 | Ng et al. | |
| 4,897,258 A | | 1/1990 | Rudy et al. | |
| 4,971,782 A | * | 11/1990 | Rudy et al. | 424/53 |
| 4,980,154 A | | 12/1990 | Gordon | |
| 5,171,564 A | * | 12/1992 | Nathoo | 424/53 |
| 5,614,174 A | * | 3/1997 | Hsu et al. | 424/53 |
| 5,648,064 A | * | 7/1997 | Gaffar et al. | 424/53 |
| 5,785,527 A | | 7/1998 | Jensen et al. | |
| 5,785,957 A | | 7/1998 | Losee et al. | |
| 5,814,304 A | | 9/1998 | Wong et al. | |
| 5,820,854 A | * | 10/1998 | Glandorf | 424/53 |
| 5,858,332 A | * | 1/1999 | Jensen et al. | 424/53 |
| 5,902,568 A | | 5/1999 | Ryles et al. | |
| 5,928,628 A | * | 7/1999 | Pellico | 424/53 |
| 5,985,249 A | | 11/1999 | Fischer | |
| 6,036,943 A | | 3/2000 | Fischer | |
| 6,086,855 A | | 7/2000 | Fischer | |
| 6,106,812 A | * | 8/2000 | Prencipe et al. | 424/53 |
| 6,162,055 A | * | 12/2000 | Montgomery et al. | 433/216 |
| 6,280,708 B1 | * | 8/2001 | Ryles et al. | 424/53 |
| 6,306,370 B1 | * | 10/2001 | Jensen et al. | 424/53 |
| 6,309,625 B1 | * | 10/2001 | Jensen et al. | 424/53 |
| 6,312,666 B1 | * | 11/2001 | Oxman et al. | 424/53 |
| 6,312,670 B1 | * | 11/2001 | Montgomery | 424/53 |
| 6,312,671 B1 | * | 11/2001 | Jensen et al. | 424/53 |
| 6,322,773 B1 | * | 11/2001 | Montgomery | 424/53 |
| 6,322,774 B1 | * | 11/2001 | Jensen et al. | 424/53 |
| 6,343,933 B1 | * | 2/2002 | Montgomery et al. | 433/216 |
| 6,365,134 B1 | * | 4/2002 | Orlowski et al. | 424/53 |
| 6,368,576 B1 | * | 4/2002 | Jensen et al. | 424/53 |

* cited by examiner

*Primary Examiner*—Shep K. Rose
(74) *Attorney, Agent, or Firm*—Knobbe Martens Olson & Bear

(57) ABSTRACT

Described herein is a novel high efficiency teeth bleaching system based on the synergetic action of the combination of hydrogen peroxide (in a free form or in the form of its adduct with urea) and peroxide and/or percarbonates of metals belonging to the first or second group of the periodic table. In one embodiment, the system of the preferred embodiment comprises two components, one containing hydrogen peroxide or carbamide peroxide (hydrogen peroxide/urea adduct), and the other containing metal peroxides and/or percarbonates. Mixing of the two components results in the accelerated generation of radical oxygen, which relates to faster teeth bleaching action.

37 Claims, No Drawings

TWO-PART COMPOSITION FOR HIGH EFFICACY TEETH WHITENING COMPRISING A MIXTURE OF PEROXIDES AND/OR PERCARBONATES OF METALS

RELATED APPLICATIONS

This application claims priority under 35 U.S.C. §119 of provisional application No. 60/234,007, filed Sep. 20, 2000.

FIELD OF THE INVENTION

This invention relates generally to teeth whiteners comprising two parts, one of which contains hydrogen peroxide (in a free form or in a form of its adduct with urea) and the other peroxides and/or percarbonates of metals belonging to the first or second group of the periodic table. More specifically, the invention relates to teeth whiteners having increased storage stability while having superior bleaching efficacy.

BACKGROUND OF THE INVENTION

Teeth whiteners, also known as teeth bleaching agents, are in widespread use as a cosmetic means to enhance appearance and, generally, to contribute to better oral health and hygiene.

Particularly popular and effective among these devices are those whose chemistry is based on peroxides, of which hydrogen peroxide and carbamide peroxide (representing an adduct of hydrogen peroxide and urea) are most frequently employed. Such peroxides are characterized by their ability to generate radical (atomic) oxygen. The chemical action of the radical/atomic oxygen is responsible for the desired whitening/bleaching effect. The generation of atomic oxygen is, however, highly undesirable during storage of such peroxide-based teeth whitening devices. Thus, in their commercial form, such devices are formulated in a manner designed to prevent and/or inhibit premature peroxide decomposition. Contact with certain foreign objects, especially materials having highly developed surface areas, certain chemicals, and elevated pH accelerate the decomposition process of said peroxides and the liberation of radical oxygen.

Stability of such teeth whitening formulations, however, is in direct conflict with the purpose and objective of their application, namely achieving the best possible whitening effect in the shortest possible time of contact with the tooth surface. Consequently, teeth whitening devices of prior art formulations typically require multiple applications stretching over a period of weeks or even months, with each recommended application time usually being from two to eight hours.

To address this conflict between stability and efficacy, two component formulations were recently developed to ensure the stability of peroxide during storage. In such formulations, the decomposition of peroxide (generation of radical oxygen) is inhibited until the two (components are mixed, these formulations allow for extended shelf life and more effective bleaching action.

In two component systems, the peroxide-containing parts are maintained at low pH and free of solid particles, conditions that are beneficial for their stability. In order to further enhance peroxide stability, special additives are used to inhibit their decomposition. Formulations based on carbamide peroxide are preferably anhydrous as the presence of water has a destabilizing effect on this compound. The second component contains materials that stimulate the decomposition of peroxides, such as alkaline substances and solid particles having highly developed surface areas. If the peroxide in the first part comprises carbamide peroxide, the medium of the second part contains water in order to minimize tissue irritation caused by the desiccating effect of anhydrous and hydrophilic mediums used in the first part.

Of the two forms of peroxides commonly used in commercial teeth whiteners, hydrogen peroxide is preferred for its greater stability, while carbamide peroxide based formulations offer advantages in terms of better compatibility with additives used to achieve more desirable consistencies and handling properties, and less risk of damage to soft tissues. Both hydrogen peroxide and carbamide peroxide-based formulations are more stable, especially the former, at low pH, preferably in the range of 3–4.5. Carbamide peroxide-based materials may, however, exhibit adequate stability even at neutral or near neutral pH. This makes such formulations more desirable in terms of better perceived compatibility with mucosa and of having no or negligible detrimental effect on tooth enamel and the health of teeth, especially those teeth which are in less than intact condition.

Carbamide peroxide formulations are particularly stable in environments containing little or no water. Examples of common commercial carriers for carbamide peroxide are glycerin and propylene glycol. While these carriers are considered nontoxic and convenient for their compatibility with desirable additives such as thickening agents, preservatives, flavors and therapeutics, their use may create some unwelcome, though generally minor, side effects. The most common is discomfort caused by their desiccating effect on mucosa, and is especially pronounced when scarified or inflamed tissue is involved. Similar responses may also be expected in cases of leaching restorations or recessed gums.

The concentrations of peroxides in commercially available teeth bleaching formulations vary greatly, generally depending on factors such as recommended time of single application, frequency and technique of application, and most significantly, the intended use: if the material is designed for professional use only, for application by the subject/patient but under professional control, or broadly available to the public for in-home, non-supervised use.

The concentration of peroxide (expressed as a percentage of $H_2O_2$) in carbamide peroxide or hydrogen peroxide based formulations sold directly to the public is generally on the order of about 3.0 to about 5.5% by weight, which corresponds to approximately 10 to 16% by weight carbamide peroxide. The concentration of $H_2O_2$ in formulations designed for professional use is often higher, in the 7–15% by weight range.

To provide prolonged contact of whitening formulation with teeth while minimizing contact with the mucosa, the whitening material is usually placed on fabricated trays, preferably ones custom procured in a dentist's office to precisely fit the patient's anatomy. The use of higher $H_2O_2$ concentration (faster-action) formulations calls for special measures to protect the mucosa from contact with such inherently irritating compositions. Rubber dams or curable tissue coatings are frequently used to protect soft tissues.

Attempts have been made to accelerate the teeth bleaching processes without increasing the concentration of the peroxide by using heat-generating devices, such as high intensity light emitting instruments or lasers. Because of the cost of necessary equipment and greatly increased risk of tissue damage associated with these techniques, they are designed for use exclusively by a dentist. The most effective of these techniques are those using lasers, but they also carry the highest risk of inflicting damage to the teeth and/or soft tissue. The cost of treatments is considerably higher than when conventional methods are used.

The shortcomings of the prior art formulations may be summarized as follows:

A) The inherent conflict between the requirements of shelf life stability of peroxides and the understandable demand for fast bleaching action and high efficacy of the product;

B) The carbamide peroxide based teeth whiteners (which are also more convenient and considered to be safer) require anhydrous or near anhydrous hydrophilic carriers for adequate storage stability which frequently cause user discomfort due to their desiccating effect on mucosa;

C) Storage stability requirements impose the necessity of maintaining low pH on commercial teeth whitening formulations, especially those based on hydrogen peroxide. This is objectionable from the point of view of the potentially damaging effect of such acidic materials on teeth and mucosa;

D) Formulations which exhibit adequate shelf life, as evidenced by maintaining stable peroxide concentrations over time, are intrinsically less effective due to the slow generation of radical (atomic) oxygen in the oral environment which impairs the speed and efficacy of the teeth bleaching process;

E) Fast acting techniques require the use of expensive, often unreliable equipment; they are also associated with increased risk to the patients and high cost per treatment. They are not designed or indicated for in-home use, but rather for application by dental professionals only.

SUMMARY OF THE INVENTION

In view of the limitations of prior art formulations, preferred embodiments of the present invention provide compositions and processes which are fast acting, non-desiccating when placed in contact with tissues, and/or are not compromised by an unduly short shelf life.

As such, in one aspect, the present invention provides a new teeth whitening system comprising two components separated from one another during storage and mixed shortly or immediately before their application to the teeth. The first part comprises 2–15% by weight hydrogen peroxide in a free form or in the form of an adduct with urea (Carbamide peroxide) dissolved or suspended in a solvent/carrier, the pH being preferably between 3.0 and 6.0. The second part of the whitening system is preferably in the form of an aqueous gel or paste and contains peroxides or percarbonates of metals belonging to the first or second group of the Periodic Table, the pH preferably being above 8.0, providing an overall pH of the mixture between 8.5 and 10.5. The accelerated bleaching of this invention is, in part, a result of the synergetic effect of the radical oxygen generating ingredients present in the first and second components. Upon mixing of the two parts, radical oxygen is generated approximately two orders of magnitude faster than it would be generated by either component separately. Further, the system of this invention allows for accomplishing the objective of highly effective teeth whitening with negligible detrimental effects on the health of hard and soft oral tissues.

DETAILED DESCRIPTION OF THE PREFERRED EMBODIMENT

As discussed above, prior art formulations for teeth whitening tend to have one or more shortcomings, rendering them ineffective or undesirable. Many of the difficulties arise from the inherent conflict between the requirements of shelf life stability of peroxides and the understandable demand for fast bleaching action and high efficacy of the product. Part of this conflict arises from the fact that storage stability requirements impose the necessity of maintaining low pH on commercial teeth whitening formulations, especially those based on hydrogen peroxide, which is objectionable because of the potentially damaging effect of such acidic materials on teeth and mucosa and the slow generation of radical (atomic) oxygen in the oral environment which impairs the speed and efficacy of the teeth bleaching process.

On the other hand, some more recent two-component bleaching formulations, containing either hydrogen peroxide or carbamide peroxide as the active ingredient require the use of highly alkaline materials to bring the pH of the final mixture above 11.0. Such alkaline materials could cause irritation of mucosa, especially in cases of scarified or inflamed tissue.

The composition disclosed herein looks to overcome some or all of the shortcomings of the prior art formulations as discussed above. In preferred embodiments, the composition provides fast acting teeth whitening compositions that minimize tissue desiccation, are substantially insensitive to ambient temperatures, and are not compromised by unduly short shelf lives.

The new teeth whitening system consists of at least two parts separated from each other during storage but mixed shortly or immediately before application. In a preferred two-component embodiment, the two components, referred to herein as Part 1 and Part 2, are preferably mixed shortly or immediately before application. Although the preferred embodiments are described and exemplified herein by means of two components, it is to be understood that the preferred embodiments are intended to cover formulations comprising more than two components. As used herein "shortly before application" means 6 to 30 minutes before application, preferably 20–30 minutes before application, and "immediately before application" means within about 5 minutes of application. The whitener may still be used more than 30 minutes after mixing, but, due to peroxide decomposition, some or most of its whitening effectiveness may be absent.

Peroxide is present in both components of the preferred embodiment, the first part comprising hydrogen peroxide in free form or as an adduct with urea, the second part comprising peroxides or percarbonates of bivalent metals preferably belonging to the first or second group of the periodic table. When mixed, the two components react synergistically to produce radical oxygen, the rate of this generation of radical oxygen being far greater than that of either part separately.

While conventionally used peroxides may be employed as active ingredients in the formulations of the preferred embodiments, the composition disclosed herein reduces the potential for damaging teeth and oral soft tissues while accelerating the teeth whitening process. This allows for shorter application times, giving results comparable to prior one-component formulations in a fraction of the time previously required.

Some important additional advantages may be realized from the herein disclosed preferred embodiments, including greatly reduced user discomfort caused by the desiccation or irritation of soft oral tissues. Also, the preferred embodiments eliminate the deleterious effects of prior art teeth whiteners on tooth enamel caused by their low or excessively high pH.

In addition, in contrast to other fast action teeth whitening systems, no special instruments are necessary or indicated in relation with the teeth whitening process disclosed herein.

The teeth whitening compositions of the preferred embodiment are composed of two integral parts: The first component of the teeth bleaching or whitening system disclosed herein contains 2–15% by weight hydrogen peroxide in free form or in the form of an adduct with urea (carbamide peroxide), including 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, and 14.5%. Preferably, if the first component is hydrogen peroxide it is between about 2 to about 6% by weight hydrogen peroxide. Preferably, if the first component is carbamide peroxide, it's concentration is between about 10% and about 32% by weight. Preferably, the pH of the first component is between about 2.5 and 6.5, including 3.0, 3.5, 4.0, 4.5, 5.0, 5.5, and 6.0. More preferably, the pH of the mixture of the first part is between about 3 and about 6. The first component may be dissolved or suspended in a suitable solvent/carrier such as water, glycerin, or propylene glycol.

Anhydrous carriers such as glycerin, ethyl alcohol and propylene glycol are preferable for formulations based on carbamide peroxide in order to achieve good chemical stability and tolerance of storage conditions. Water is the primary solvent for formulations based on hydrogen peroxide, which allows for a broader selection of thickeners. Such thickeners may include, in addition to polyacrylic acid and its derivatives, xantham gum, polyalkylene oxides, polyglycols, and cellulose derivatives. Preferably the glycerin concentration is from about 20 to about 90%. Even more preferably, the glycerin concentration is from about 40 to about 85%.

Suitable thickeners may be added to such blends to achieve a desirable consistency to facilitate application and to slow the dissolution process in order to prolong the bleaching action. Polycarboxylic acid and its salts are preferred thickeners for first part formulations based on carbamide peroxide.

Thickeners used for hydrogen peroxide based compositions, may include, in addition to polyacrylic acid and its derivatives, xantham gum, polyalkylene oxides, polyglycols, and cellulose derivatives.

The second part contains 2–50% by weight peroxides or percarbonates of metals belonging to the first or the second group of the periodic table, including 5%, 6%, 7%, 8%, 9%, 10%, 12%, 14%, 16%, 18%, 20%, 25%, 27%, 30%, 32%, 35%, 36%, 38%, 40%, 44%, and 48%. It is to be understood that the second group is used herein to refer to elements of Group 2a and 2b of the periodic table of the elements. In a further embodiment, the second part contains 13–34% by weight peroxides or percarbonates of metal belonging to the first or second group of the periodic table or mixtures therein. The peroxides or percoarbonates of metals belonging to the first or second group of the periodic table may include calcium peroxide, zinc peroxide, calcium percarbonate, zinc percarbonate, strontium peroxide or percarbonate, and magnesium peroxide or percarbonate.

The second part is preferably of a paste consistency by using thickening and suspending agents. Common thickening and suspending agents may be used to optimize the consistency of the second part of the teeth bleaching systems disclosed herein. Preferred thickening agents are polyacrylic acid and its derivatives, polyglycols, polyalkylene oxides, cellulose derivatives, water-soluble natural gums, gelatin and starch, calcium carbonate, calcium silicate, sodium and calcium phosphates, silica, and Bentonite. If the system of the preferred embodiments is intended for application with a toothbrush, certain abrasive agents such as pumice and aluminum oxide may also be incorporated in the second component.

Preferably, the second part or component has a pH of greater than 8.5, including 9, 9.5, 10, 10.5, 11, 11.5, 12, 12.5, 13, 13.5, and 14. Water, glycerin, propyleneglycol or polyglycols may serve as principle mediums in which metal peroxides are suspended. Glycerin may serve as a principle medium in which metal percarbonates are suspended.

Because of the accelerating effect of the second part on generation of radical oxygen, the first component of the system may also contain periodic stabilizers to enhance their stability at adverse storage conditions. Such stabilizers may include iodium pyrophosphate and i-hydroxyethyliolene-1, 1-phosphonic acid.

Incorporation of fluoride salts such as stannous fluoride, sodium monofluorophosphate or sodium fluoride may add additional benefits to the teeth treatments of the preferred embodiments and may be added to the first part, the second part, or both.

Flavoring and coloring agents may be added to enhance the acceptance or appeal of either or both parts, or as indicators of the reactivity of peroxide and the progress of radical oxygen generation. The most desirable flavors may include, among others, food grade orange, lemon, peppermint, spearmint, mint, bubble gum, cherry, watermelon, strawberry and apple varieties. As coloring agents FD&C or FD&C water soluble dyes may be used; FD&C Blue #1 and FD&C Blue #2 are preferred. Coloring and/or flavoring agents are preferably, but not necessarily, incorporated into the second part of the system.

The composition containing both parts, may be left on the teeth for a time long enough to allow for the bleaching effect. Preferably, the composition is left on 2–180 minutes, including 5, 8, 12, 15, 18, 20, 24, 25, 28, 35, 38, 40, 50, 60, 70, 80, 90, 100, 120, 150, and 170 minutes. In a further embodiment, the composition may be left on the teeth for 10–30 minutes.

Preferably, the composition containing both parts is at a pH of between about 7 and 12, including 7.0, 7.5, 8.0, 8.5, 9, 9.5, 10, 10.5, 11, and 11.5. More preferably, the composition containing both parts is at a pH of between about 8.5 and 10.5.

In the examples, preferred embodiments were tested and it was unexpectedly found that in a system comprising two different types of peroxy compounds, one being hydrogen peroxide in either free form or in the form of an adduct and the other peroxides or percarbonates of metals belonging to the first or second group of the periodic table, a synergistic effect occurred when the two were mixed, resulting in the more efficient and controllable release of radical oxygen. The result of such synergy is a dramatically accelerated teeth bleaching effect unachievable by either such peroxides applied separately.

In the following examples, the blends of Part A and Part B are prepared as follows: the components soluble in mediums (i.e., soluble in propylene glycol or water) are typically introduced first. After they are completely dissolved the insoluble ingredients are introduced. The mixers are of the conventional type. The two components, Part A and B can be mixed together in many ways depending on the chosen dispensing system for the commercial form of the merchandise. Two of the most popular dispensing systems are so-called static mixers (elongated tips with a screw-type insert) and blending with a spatula on a mixing pad.

The following examples use decolorization of FD&C blue coloring #1 to exhibit the decolorization action of the teeth bleaching mixtures. After Parts 1 and 2 are mixed, decolorization of the FD&C blue is monitored. In one embodiment, these dyes are added to the preparations to monitor how long the patient needs to leave the preparation in contact with his/her teeth. When the blue color disappears or is substantially reduced by the dye, the patient can assume that the teeth bleaching activity has occurred.

EXAMPLES

Example 1
Part 1

| | |
|---|---|
| * glycerin | 54.5 g |
| * water | 27.58 g |
| * polyethylene oxide (MW 400,000) | 14.0 g |
| * hydrogen peroxide | 4.0 g |
| * sodium pyrophosphate | 0.1 g |

Part 2

| | |
|---|---|
| * glycerin | 42.4 g |
| * calcium peroxide | 28 5 g |
| * water | 16.8 g |
| * silica | 6.5 g |
| * zinc peroxide | 4.9 g |
| * carboxymethyl cellulose | 0.9 g |

The two components were mixed in a 1:1 ratio by weight. The pH of the mixture was 12 at 26.5° C. When 1 drop of FD&C Blue #1 was added, the color disappeared entirely within 8 minutes.

Example 2
Part 1
Same as in Example 1
Part 2

| | |
|---|---|
| * glycerin | 44.9 g |
| * calcium peroxide | 30.2 g |
| * water | 17.75 g |
| * silica | 6.25 g |
| * carboxymethyl cellulose | 0.9 g |

The pH of a 1:1 mixture was 10.5 at 26.5° C. The color from 1 drop of FD&C Blue #1 disappeared within 10 minutes.

Example 3
Part 1
Same as in Example 1
Part 2

| | |
|---|---|
| * glycerin | 53.8 g |
| * water | 21.4 g |
| * calcium peroxide | 19.0 g |
| * silica | 5.0 g |
| * | |

The pH of a 1:1 mixture by weight was 10.23 at 25.9° C. The color from 1 drop of FD&C Blue #1 discolored within 20 minutes.

Example 4
Part 1

| | |
|---|---|
| * glycerin | 86.0 g |
| * carbamide peroxide | 11.0 g |
| * partially neutralized polyacrylic acid | 3.0 g |

Part 2
Same as in Example 3
The pH of a 1:1 mixture by weight was 9.72 at 25.4° C. When 1 drop of FD&C Blue #1 was added, the discoloration time was between 15 and 20 minutes.

Example 5
Part 1

| | |
|---|---|
| * glycerin | 84.3 g |
| * carbamide peroxide | 13 g |
| * partially neutralized polyacrylic acid | 2.7 g |

Part 2
Same as in Example 3
When the two components were mixed in a 1:1 ratio by weight, the pH was 9.75 at 25.6° C. when 1 drop of FD&C Blue #1 was added, the mixture discolored in between 15 and 20 minutes.

Example 6
Part 1
Same as in Example 1
Part 2

| | |
|---|---|
| * glycerin | 55.7 g |
| * calcium peroxide | 12.9 g |
| * water | 22.2 g |
| * silica | 7.7 g |
| * carboxymethyl cellulose | 1.1 g |
| * sodium percarbonate | 0.3 g |

The pH of a 1:1 mixture by weight was 10.8 at 27.6° C.; the discoloration time of one drop of FD&C Blue #1 was added was 15 minutes.

Although the compositions and method disclosed herein have been described in terms of certain preferred embodiments, other embodiments will become apparent to those of skill in the art in view of the disclosure and claims herein. Thus, obvious changes and modifications may be made without departing from the spirit and scope of the preferred embodiments. Accordingly, the scope of the invention is not intended to be limited by the foregoing, but rather to be defined only by the claims which follow.

What is claimed is:
1. A teeth whitening composition comprising:
   Part 1 comprising peroxide in free form or the form of an adduct with urea; and
   Part 2 comprising peroxides and/or percarbonates of bivalent metals;
   wherein Part 1 and Part 2 are mixed together shortly or immediately before application to form a blend having a pH of about 7 to about 12.
2. The teeth whitening composition of claim 1 wherein said peroxides and/or percarbonates of bivalent metals belong to the second group of the periodic table.

3. The teeth whitening composition of claim 1 wherein said pH is between about 8.0 and about 11.

4. The teeth whitening composition of claim 1 wherein said pH is between about 8.5 and about 10.5.

5. The composition of claim 1 wherein said peroxide in Part 1 is hydrogen peroxide.

6. The composition of claim 5, wherein the concentration of hydrogen peroxide in Part 1 is from about 2 to about 15% by weight.

7. The composition of claim 1 wherein the peroxide in Part 1 comprises carbamide peroxide.

8. The composition of claim 6 wherein the concentration of carbamide peroxide in Part 1 is from about 10 to about 40% by weight.

9. The composition of claim 1 wherein the pH of Part 1 is between about 2.5 and about 6.5.

10. The composition of claim 1 wherein the pH of Part 2 is between about 8.0 and about 14.

11. The composition of claim 1 wherein Part 1 further comprises one or more flavoring agents.

12. The composition of claim 1 wherein Part 2 further comprises one or more flavoring agents.

13. The composition of claim 11, wherein said flavoring agents are selected from the group consisting of: orange, lemon, peppermint, spearmint, mint, bubble gum, cherry, watermelon, strawberry and apple varieties.

14. The composition of claim 1 wherein Part 1 and/or Part 2 further comprises colorants.

15. The composition of claim 13 wherein Part 2 further comprises one or more coloring agents.

16. The composition of claim 1 wherein Part 1 and/or Part 2 further comprises a dye susceptible to discoloration when exposed to radical oxygen.

17. The composition of claim 15 wherein said dye is FD&C Blue #1 and/or FD&C Blue #2.

18. The composition of claim 1 wherein Part 1 and/or Part 2 further comprises fluorides.

19. The composition of claim 18 wherein said fluoride is selected from the group consisting of sodium fluoride, stannous fluoride, and sodium monofluorophosphate.

20. The composition of claim 18 wherein the concentration of said fluoride component(s) is from about 100 to about 2,000 ppm.

21. The composition of claim 1 wherein the water concentration in the mixture of Parts 1 and 2 is about 10 to about 60% by weight.

22. The composition of claim 1 wherein Part 1 and/or Part 2 further comprises thickening agents.

23. The composition of claim 22, wherein said thickening agents are selected from the group consisting of: polyacrylic acid, polyacrylic acid salts, the reaction products of polyacrylic acids with amines, natural gums, cellulose derivatives, and polyalkylene oxides.

24. The composition of claim 1 wherein Part 2 comprises calcium peroxide at a concentration of about 2 to about 50% by weight.

25. The composition of claim 1 in which Part 2 comprises magnesium peroxide at a concentration of about 2 to about 30% by weight.

26. The composition of claim 1 wherein Part 2 comprises at least one peroxide selected from the group consisting of: calcium, zinc, strontium, magnesium and mixtures thereof.

27. The composition of claim 1, wherein the total peroxide concentration of Part 2 is between about 2 and 50% by weight.

28. The composition of claim 1 wherein Part 2 further comprises mild abrasives.

29. The composition of claim 28, wherein said abrasives are selected from the group consisting of: calcium carbonate, calcium silicate, calcium phosphates, fumed silica, precipitated silica, diatomaceous earth, pumice, and Bentonite.

30. A teeth whitening procedure, comprising:
    preparing a teeth whitening composition comprising at least two parts: a Part 1, comprising hydrogen peroxide in free form or the form of an adduct with urea and a Part 2, comprising peroxides and/or percarbonates of metals belonging to the second group of the periodic table; wherein Part 1 and Part 2 are mixed together shortly or immediately before application to form a material having a pH from about 8.5 to about 10.5; and
    contacting the teeth whitening composition with the teeth for a time sufficient to increase the whiteness of the teeth.

31. The teeth whitening procedure of claim 30, wherein the teeth whitening composition is applied to the teeth by means of flexible trays or forms.

32. The teeth whitening procedure of claim 30, wherein the teeth whitening composition is applied to the teeth by means of a toothbrush.

33. The teeth whitening procedure of claim 30, wherein the teeth whitening composition is applied to the teeth by means of the freehand technique.

34. The teeth whitening procedure of claim 30, wherein the teeth whitening composition is in the form of an oral rinse or gargle.

35. The teeth whitening procedure of claim 30, wherein the teeth whitening composition is applied in one or more sessions, each session lasting about 2 to about 180 minutes.

36. The teeth whitening procedure of claim 30, wherein the teeth whitening composition is applied in one or more sessions, each session lasting about 2 to about 30 minutes.

37. A teeth whitening composition comprising:
    Part 1 comprising peroxide in free form or the form of an adduct at a concentration of about 2 to about 15% by weight hydrogen peroxide; and
    Part 2 comprising peroxides and/or percarbonates of metals belonging to the second group of the periodic table, wherein said metal is selected from the group consisting of calcium, zinc, strontium, and magnesium at a concentration of about 2 to about 50% by weight; and
    wherein Part 1 and Part 2 are mixed together shortly or immediately before application to form a blend having a pH of about 7.5 to about 12.

* * * * *